(12) United States Patent
Khalighi et al.

(10) Patent No.: US 11,672,492 B2
(45) Date of Patent: Jun. 13, 2023

(54) FEATURE SPACE BASED MR GUIDED PET RECONSTRUCTION

(71) Applicant: The Board of Trustees of the Leland Stanford Junior University, Stanford, CA (US)

(72) Inventors: Mohammad Mehdi Khalighi, San Jose, CA (US); Michael E. Moseley, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 325 days.

(21) Appl. No.: 17/098,376

(22) Filed: Nov. 14, 2020

(65) Prior Publication Data

US 2021/0150782 A1     May 20, 2021

Related U.S. Application Data

(60) Provisional application No. 62/935,983, filed on Nov. 15, 2019.

(51) Int. Cl.
| | |
|---|---|
| *A61B 6/03* | (2006.01) |
| *G06T 11/00* | (2006.01) |
| *G06F 18/213* | (2023.01) |
| *G06V 10/77* | (2022.01) |

(52) U.S. Cl.
CPC ............ *A61B 6/037* (2013.01); *G06F 18/213* (2023.01); *G06T 11/006* (2013.01); *G06T 11/008* (2013.01); *G06V 10/7715* (2022.01)

(58) Field of Classification Search
None
See application file for complete search history.

(56) References Cited

U.S. PATENT DOCUMENTS

| | | | |
|---|---|---|---|
| 2012/0179021 A1* | 7/2012 | Blevis | A61B 6/037 600/407 |
| 2014/0126793 A1* | 5/2014 | Ahn | G06T 11/006 382/131 |
| 2019/0172570 A1* | 6/2019 | Popescu | G16H 10/60 |
| 2020/0151880 A1* | 5/2020 | Stayman | G06T 7/0016 |

OTHER PUBLICATIONS

Ellis, Sam, and Andrew J. Reader. "Penalized maximum likelihood simultaneous longitudinal PET image reconstruction with difference-image priors." Medical Physics 45.7 (2018): 3001-3018. (Year: 2018).*

(Continued)

*Primary Examiner* — Michelle M Entezari
(74) *Attorney, Agent, or Firm* — Lumen Patent Firm

(57) ABSTRACT

A method for PET image reconstruction acquires PET data by a PET scanner; reconstructs from the acquired PET data a seed PET image; builds a feature space from the seed PET image and anatomical images co-registered with the seed PET image; performs a penalized maximum-likelihood reconstruction of a PET image from the seed PET image and the feature space using a penalty function that is calculated based on the differences between each voxel and its neighbors both on the PET image and in the feature space regardless of their location in the image.

5 Claims, 6 Drawing Sheets

(56) References Cited

OTHER PUBLICATIONS

Bland, J., Mehranian, A., Belzunce, M. A., Ellis, S., da Costa-Luis, C., McGinnity, C. J., . . . & Reader, A. J. (2019). Intercomparison of MR-informed PET image reconstruction methods. Medical physics, 46(11), 5055-5074 (Received Jan. 13, 2019; published Oct. 4, 2019) (Year: 2019).*
Wang G, Qi J. PET image reconstruction using kernel method. IEEE transactions on medical imaging. Jul. 30, 2014;34(1):61-71. (Year: 2014).*
Hutchcroft W, Wang G, Chen KT, Catana C, Qi J. Anatomically-aided PET reconstruction using the kernel method. Physics in Medicine & Biology. Aug. 19, 2016;61(18):6668. (Year: 2016).*
Bland J, Belzunce MA, Ellis S, McGinnity CJ, Hammers A, Reader AJ. Spatially compact MR-guided kernel EM for PET image reconstruction. IEEE transactions on radiation and plasma medical sciences. Jun. 6, 2018;2(5):470-82. (Year: 2018).*
Filipović M, Barat E, Dautremer T, Comtat C, Stute S. PET reconstruction of the posterior image probability, including multimodal images. IEEE transactions on medical imaging. Dec. 9, 2018;38(7):1643-54. (Year: 2018).*
Lantos J, Mittra ES, Levin CS, and Iagaru A, "Standard OSEM vs. regularized PET image reconstruction: qualitative and quantitative comparison using phantom data and various clinical radiopharmaceuticals," Am J Nucl Med Mol Imaging. 2018; 8(2): 110-118.

Spangler-Bickell M, Khalighi MM, Hoo C, et al., "Rigid Motion Correction for Brain PET/MR Imaging Using Optical Tracking," IEEE Tran on Radiation and Plasma Medical Sciences 3 (4), 498-503.
Bowsher J E, et al. Utilizing MRI information to estimate F18-FDG distributions in rat flank tumors IEEE Nuclear Science Symp. and Medical Imaging Conf. pp. 2488-2492, 2004.
Bai B, et al. MR Guided PET Image Reconstruction. Semin Nucl Med. Jan. 2013; 43(1): 30-44.
Passalaqua S, et al. Qualitative and quantitative evaluation of regularized PET image reconstruction. Journal of Nuclear Medicine. 2014;55(supplement 1):579-579.
Ahn S, et al. Quantitative comparison of OSEM and penalized likelihood image reconstruction using relative difference penalties for clinical PET. Physics in Medicine & Biology. 2015;60(15):5733.
Sah BR, et al. Clinical evaluation of a block sequential regularized expectation maximization reconstruction algorithm in 18F-FDG PET/CT studies. Nuclear medicine communications. 2017;38(1):57-66.
Teoh EJ, et al. Phantom and clinical evaluation of the Bayesian penalized likelihood reconstruction algorithm Q. Clear on an LYSO PET/CT system. Journal of Nuclear Medicine. 2015;56(9):1447-1452.
Qi J, et al. Iterative reconstruction techniques in emission computed tomography. Phys Med Biol. 2006;51(15):R541-578.
Hudson et al., Accelerated image reconstruction using ordered subsets of projection data. IEEE Trans Med Imaging. 1994;13(4):601-609.

* cited by examiner

*Fig. 4A*
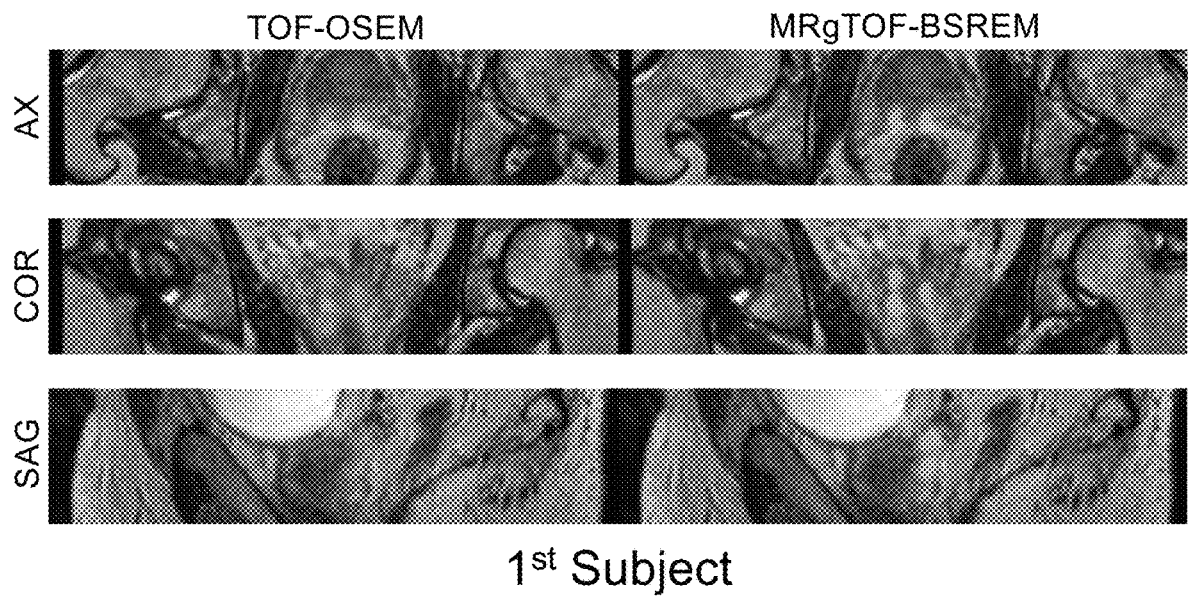
1st Subject
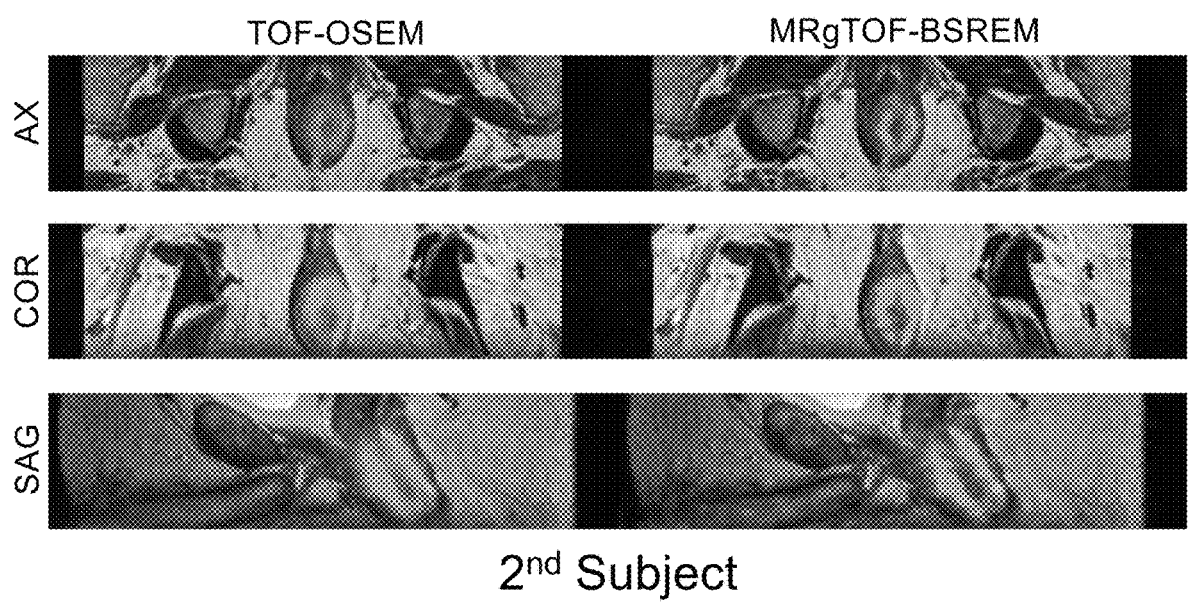
2nd Subject
*Fig. 4B*

FEATURE SPACE BASED MR GUIDED PET RECONSTRUCTION

CROSS-REFERENCE TO RELATED APPLICATIONS

This application claims priority from U.S. Provisional Patent Application 62/935,983 filed Nov. 15, 2019, which is incorporated herein by reference.

FIELD OF THE INVENTION

The present invention relates generally to PET medical imaging. More specifically, it relates to PET image reconstruction techniques.

BACKGROUND OF THE INVENTION

Ordered subset expectation maximization (OSEM) disclosed in Hudson et al., *IEEE Trans Med Imaging.* 1994; 13(4):601-609 is one of the most common PET image reconstruction methods used in clinical practice. It has a superior image quality relative to analytical reconstruction methods; however, in order to control the image noise, it is stopped early, and post filtering is applied. An alternative set of PET reconstruction algorithms based on the penalized maximum-likelihood (PML) method disclosed in Qi J, et al. *Phys Med Biol.* 2006; 51 (15): R541-578 use a penalty function, which controls for image quality, and adds it to a cost function, which is minimized by iterative reconstruction, allowing users to control the trade-off between noise and image resolution by adjusting a single parameter. One type of PML image reconstruction algorithm that uses the relative difference penalty as disclosed in Teoh E J, et al. *Journal of Nuclear Medicine.* 2015; 56(9):1447-1452 is block sequential regularized expectation maximization (BSREM), where the beta value controls the trade-off between image quality and resolution. BSREM is described in Sah B R, et al. *Nuclear medicine communications.* 2017; 38(1):57-66. Ahn S, et al. *Physics in Medicine & Biology.* 2015; 60(15):5733. Passalaqua S, et al. *Journal of Nuclear Medicine.* 2014; 55 (supplement 1):579-579.

The spatial resolution of PET images is limited by the intrinsic resolution of the detectors. One approach to improving PET image spatial resolution is to use anatomical information from other imaging modalities, such as Computed Tomography or Magnetic Resonance, within the PET reconstruction algorithm disclosed in Bai B, et al. M R Guided PET Image Reconstruction. Semin Nucl Med. 2013 January; 43(1): 30-44. These methods use the anatomical image as a priori knowledge to modify the penalty function of a PML reconstruction method. For instance, in the Bowsher method disclosed in Bowsher J E, et al. IEEE Nuclear Science Symp. and Medical Imaging Conf. pp 2488-92, 2004, the local differences of each image voxel with its most similar neighbors from the anatomical image is calculated to update the penalty function. These methods use the anatomical information in image space e.g. looking at the neighboring voxel intensity or the boundaries between different anatomical regions.

Current PET reconstruction methods using anatomical priors use the image space to enforce the similarity between the neighboring voxels in anatomical images. These methods are generally vulnerable to mismatches between the anatomical image and the true activity distribution and may either mask the molecular information or create non-existing abnormalities by enforcing anatomical boundaries from the MR images. In these methods, anatomical information alone can force the image formation and result in mismatches between the anatomical images and the true activity. These MR-guided PET reconstruction methods thus have to choose their weighting functions carefully so that they do not mask the PET information or create non-existing abnormalities by using anatomical images.

BRIEF SUMMARY OF THE INVENTION

The present invention provides a penalized maximum-likelihood (PML) reconstruction method for PET images using anatomical images as a priori knowledge. Significantly, it uses the anatomical information in the feature space rather than the image space. The anatomical information may include functional images.

The technique modifies BSREM to use the Magnetic Resonance (MR) anatomical images that are acquired simultaneously with PET data on a PET/MR scanner to improve the spatial resolution of PET images.

In one aspect, the invention provides a method for PET image reconstruction comprising: acquiring PET data by a PET scanner; reconstructing from the acquired PET data a seed PET image; building a feature space from the seed PET image and anatomical images co-registered with the seed PET image; performing a penalized maximum-likelihood reconstruction of a PET image from the seed PET image and the feature space using a penalty function calculated based on the differences between each voxel and its neighbors both on the PET image and in the feature space (regardless of their location in the image).

In some implementations, building a feature space comprises mapping values of voxels into an (N+1)-dimensional space, where N is a number of sets of the anatomical images. In some implementations, the penalty function is a combination of a first PL objective function calculated using a relative difference prior method on neighboring voxels in image space and a second PL objective function using the relative difference prior method on neighboring voxels in the feature space. In some implementations, the anatomical images are computed tomography images or magnetic resonance images. In some implementations, reconstructing the seed PET image uses OSEM PET reconstruction.

Applications of the method include Positron Emission Tomography (PET) and PET image reconstruction. Advantages and improvements over existing methods include improving the spatial resolution of PET images using anatomical images as a priori knowledge.

BRIEF DESCRIPTION OF THE SEVERAL VIEWS OF THE DRAWINGS

FIG. 4A is an image grid for a first subject, comparing fused PET and MR prostate images using the conventional TOF-OSEM and MRgTOF-BSREM.

FIG. 4B is an image grid for a second subject, comparing fused PET and MR prostate images using the conventional TOF-OSEM and MRgTOF-BSREM.

DETAILED DESCRIPTION OF THE INVENTION

The resolution of PET images is limited by several physical factors, including positron range, scatter, and the finite size of the detector elements. The current spatial resolution of PET images is ~4 mm for whole body PET/MR. Anatomical MR images with higher resolution and superior SNR have been used in PET reconstruction to improve the image quality and spatial resolution. However, these methods are generally vulnerable to mismatches between the anatomical image and the true activity distribution. To address this problem, the present invention provides a feature-based approach to incorporate anatomical priors in PET image reconstruction, where the location of a voxel or its neighbors in image space does not play a direct role, and where both functional and anatomical images are used to construct the feature space.

Figure 5:
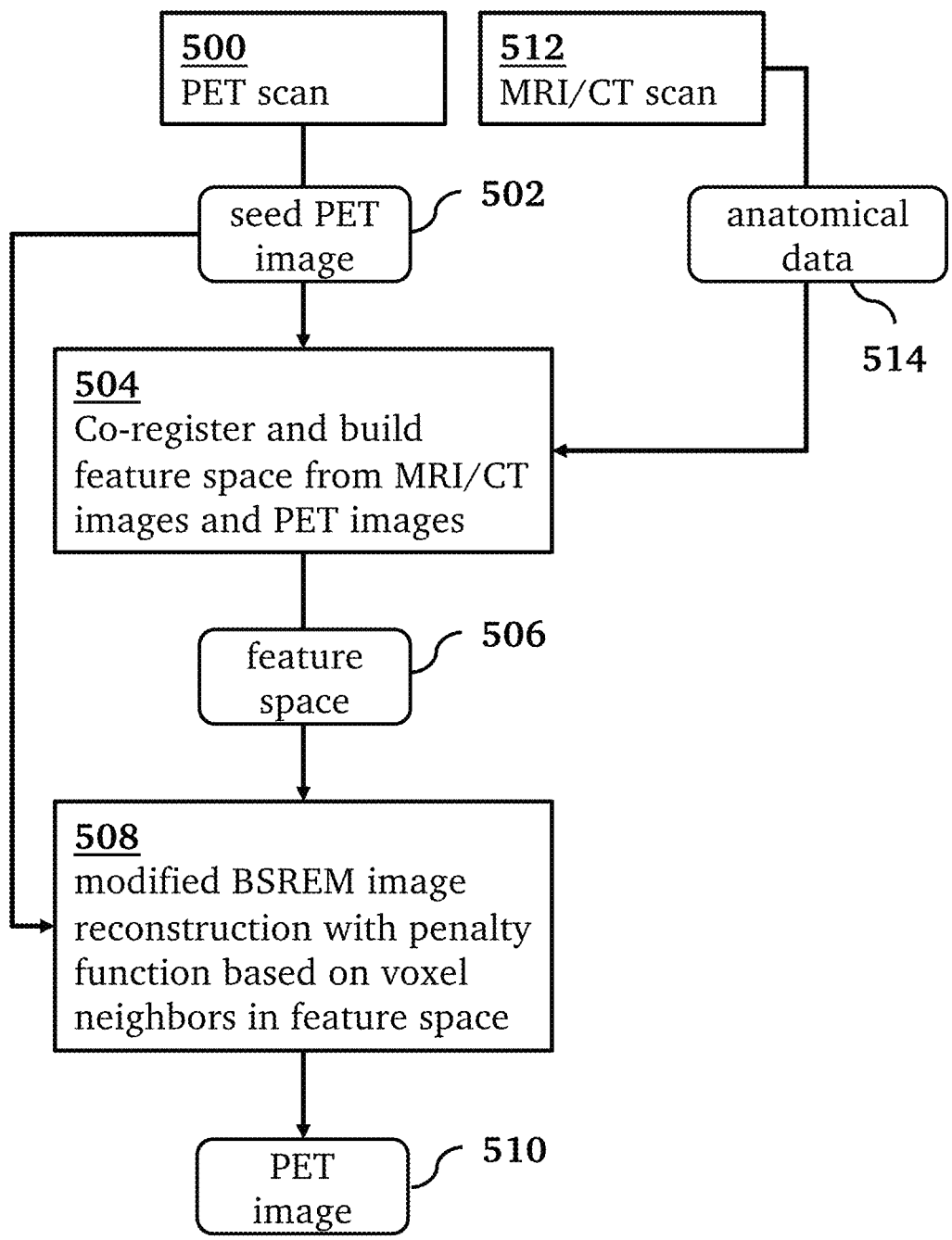
FIG. 5 is an overview of a processing pipeline for a method for PET image reconstruction, according to an embodiment of the invention.

An overview of a method for PET image reconstruction, according to an embodiment of the invention, is shown in FIG. 5. In this method, an MRI scan 512 generates anatomical data 514 in the form of MRI images (e.g. T1-weighted, T2-weighted). A PET scan 500 using an original OSEM PET reconstruction generates a seed PET image 502. In step 504 the anatomical data 514 and seed PET image 502 are co-registered and used to form the feature space 506. Then, a modified BSREM image reconstruction 508 generates a reconstructed PET image 510 from the seed PET image 502 using the feature space 506. The reconstruction 508 uses a penalty function calculated based on the differences between each voxel and its neighbors in the feature space regardless of their locations in the image space. We call this technique MR-guided block sequential regularized expectation maximization, or MRgBSREM. By combining the relative difference priors with anatomical priors in a penalized maximum likelihood PET reconstruction algorithm, the signal to noise ratio (SNR) is improved in the reconstructed images. By adding a seed PET image to the anatomical priors, a mismatch between the true activity distribution and other anatomical priors is avoided. That is, by using an initial OSEM PET, it is guaranteed that the anatomical information alone cannot force the image formation and therefore it will be immune to mismatches between the anatomical images and the true activity.

Figure 1A:
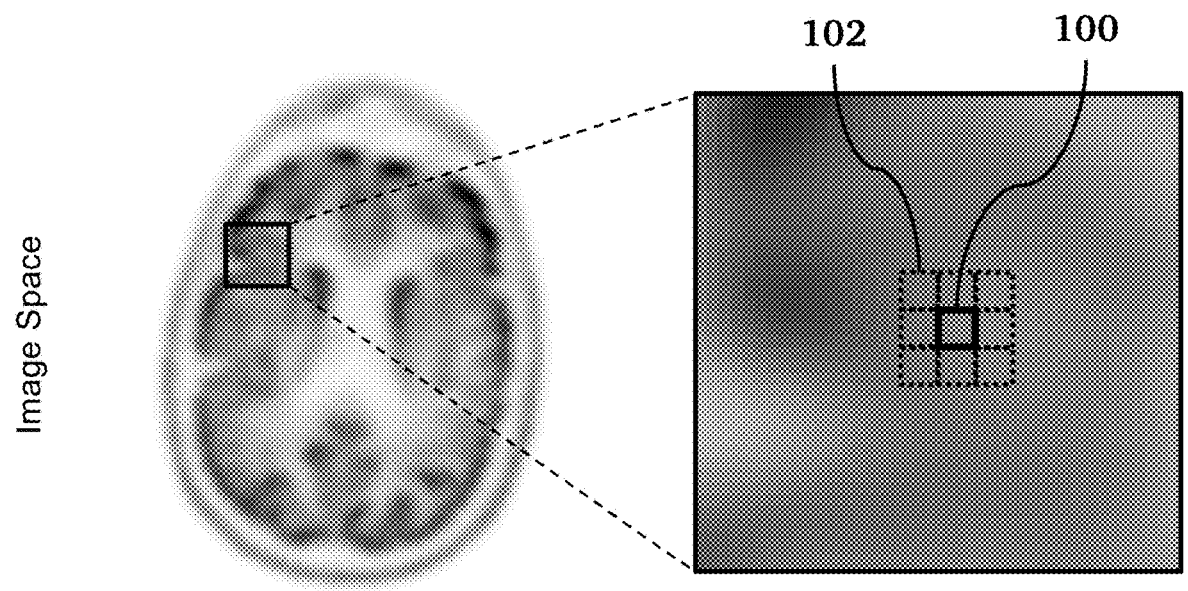
FIG. 1A shows a typical voxel and its neighboring voxels in image space, where their local differences in voxel activity are used to calculate the penalty in the cost function of BSREM method.

The PET reconstruction technique of the present invention adapts a penalized maximum-likelihood algorithm based on the relative difference prior (RDP), which uses a block sequential regularized expectation maximization (BS-REM) optimizer. Conventionally, the RDP applies activity-dependent smoothing to control noise at higher iterations and suppresses image noise in low-activity background regions. This relative difference penalty is calculated based on the difference in image space between each voxel activity and its neighboring voxels, as shown in FIG. 1A. The figure shows a typical voxel 100 and its neighboring voxels 102 where their local differences in voxel activity are used to calculate the penalty in the cost function of a conventional BSREM method.

Figure 1B:
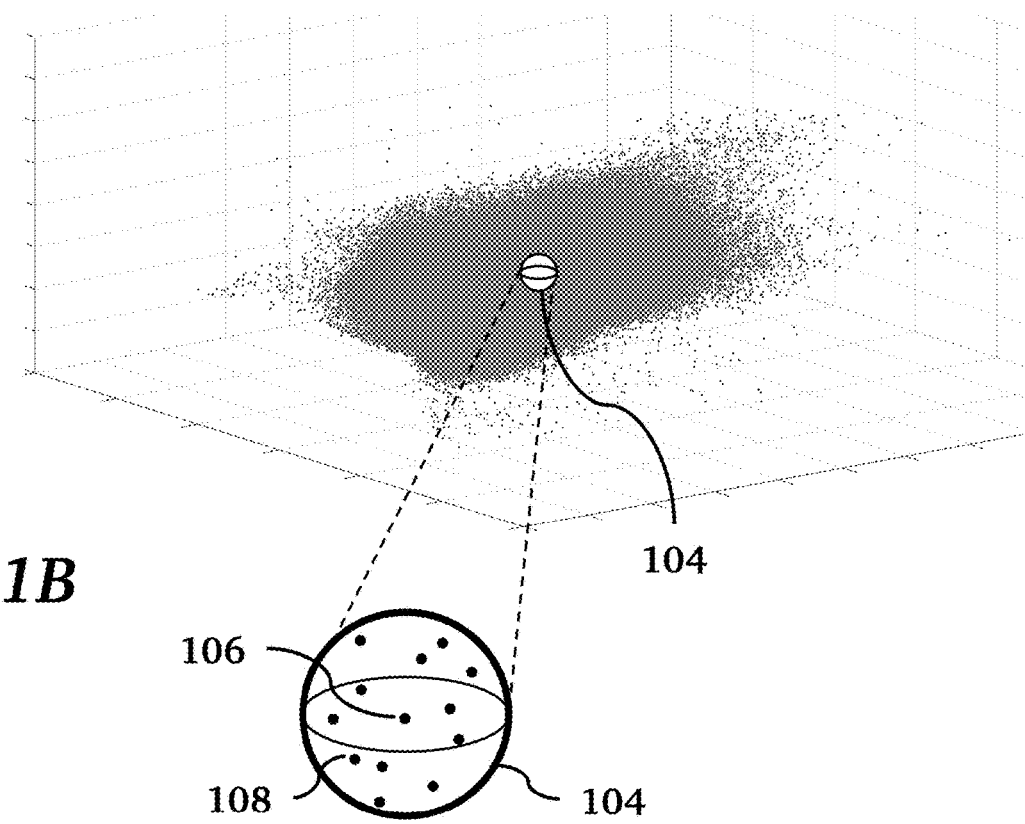
FIG. 1B shows a feature space constructed with normalized FLAIR, CUBE and PET image datasets, where the neighborhood around a voxel is used to calculate an additional penalty to the cost function.

In the present invention, a new penalty based on the relative differences between each voxel 104 and its neighboring voxels in both the feature space and image space was calculated and used in the BSREM reconstruction method. We have used the same framework to incorporate the MR anatomical priors into the image reconstruction by applying an additional penalty, which is calculated based on the relative difference between each voxel activity and its neighboring voxels in the feature space, as shown in FIG. 1B. The figure shows the feature space constructed with normalized FLAIR, CUBE and PET image datasets. Each dot represents a voxel in the image space. The sphere 104 shows the neighborhood of voxels 108 around a typical voxel 106. An additional penalty to the cost function is based on the activity differences between the typical voxel 106 and voxels 108 contained in its feature-space neighborhood 104. Thus, the penalty function considers both the relative differences between similar voxels in feature space in addition to adjacent voxels in image space. Similar voxels are identified by their proximity in the feature space (which is created by MR images and a Seed PET image). The seed PET image and co-registered MR images were normalized and mapped to a 3D feature space where each voxel was represented by a point.

The feature space is constructed based on all co-registered multi-parametric functional or anatomical MRI images and an initial PET reconstruction. The feature space construction may use a conventional OSEM algorithm. By including the conventional PET reconstructed images in the feature space, the mismatches between the anatomical priors and true activity distribution will not affect the final image.

Example 1

The techniques of the present invention and its advantageous results are illustrated in the following example. In the first example, subjects were injected with 8 mCi of FDG and underwent a 60-minute brain scan on a SIGNA PET/MR (GE Healthcare, Waukesha, Wis.). 3D T1 IR FSPGR, 3D T2 CUBE and 3D T2 FLAIR CUBE images were acquired simultaneously with PET. The seed PET images were reconstructed with TOF-OSEM with both 2.78 mm and 1.17 mm slice thickness and a transaxial pixel size was 1.17 mm$^2$ (256×256 matrix on a 30 cm FOV). They were also reconstructed using the anatomical priors, i.e., 3D T1, 3D T2 and 3D FLAIR images with MR guided TOF-BSREM (MRgTOF-BSREM) using iso-tropic 1.17 mm$^3$ resolution.

Figure 2:
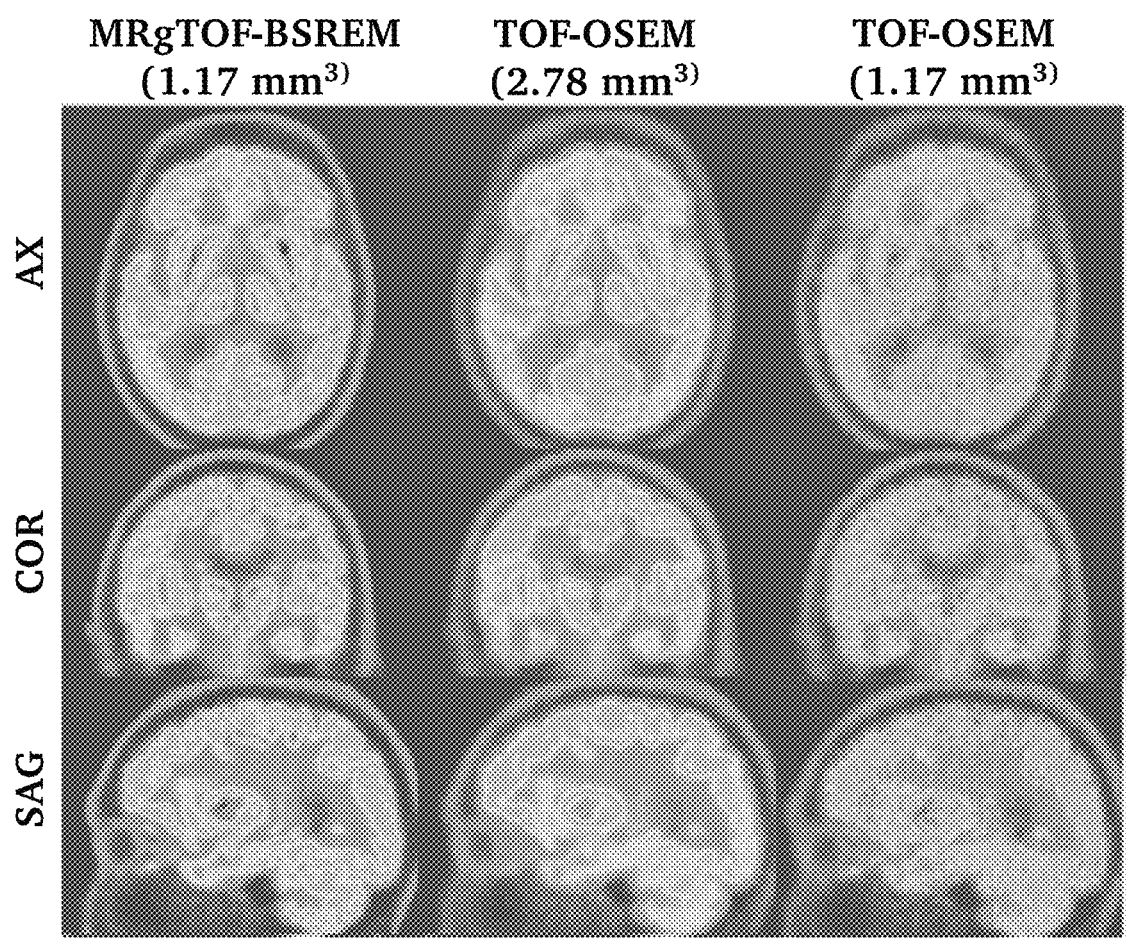
FIG. 2 is an image grid comparing images reconstructed by MRgTOF-BSREM images reconstructed by conventional TOF-OSEM with two slice thicknesses.

FIG. 2 shows the comparison between high resolution isotropic images with 1.17 mm slice thickness reconstructed by MRgTOF-BSREM and TOF-OSEM (left and right columns, respectively) as well as the conventional TOF-OSEM reconstruction with 2.78 mm slice thickness (center column). Sagittal (SAG), coronal (COR), and axial (AX) views are shown for each. As expected, the high-resolution images reconstructed by TOF-OSEM have lower signal to noise (SNR) ratio and do not show the anatomical boundaries well. In contrast, the MRgTOF-BSREM show an improved SNR and a detailed anatomical boundary compared to TOF-OSEM.

Figure 3:
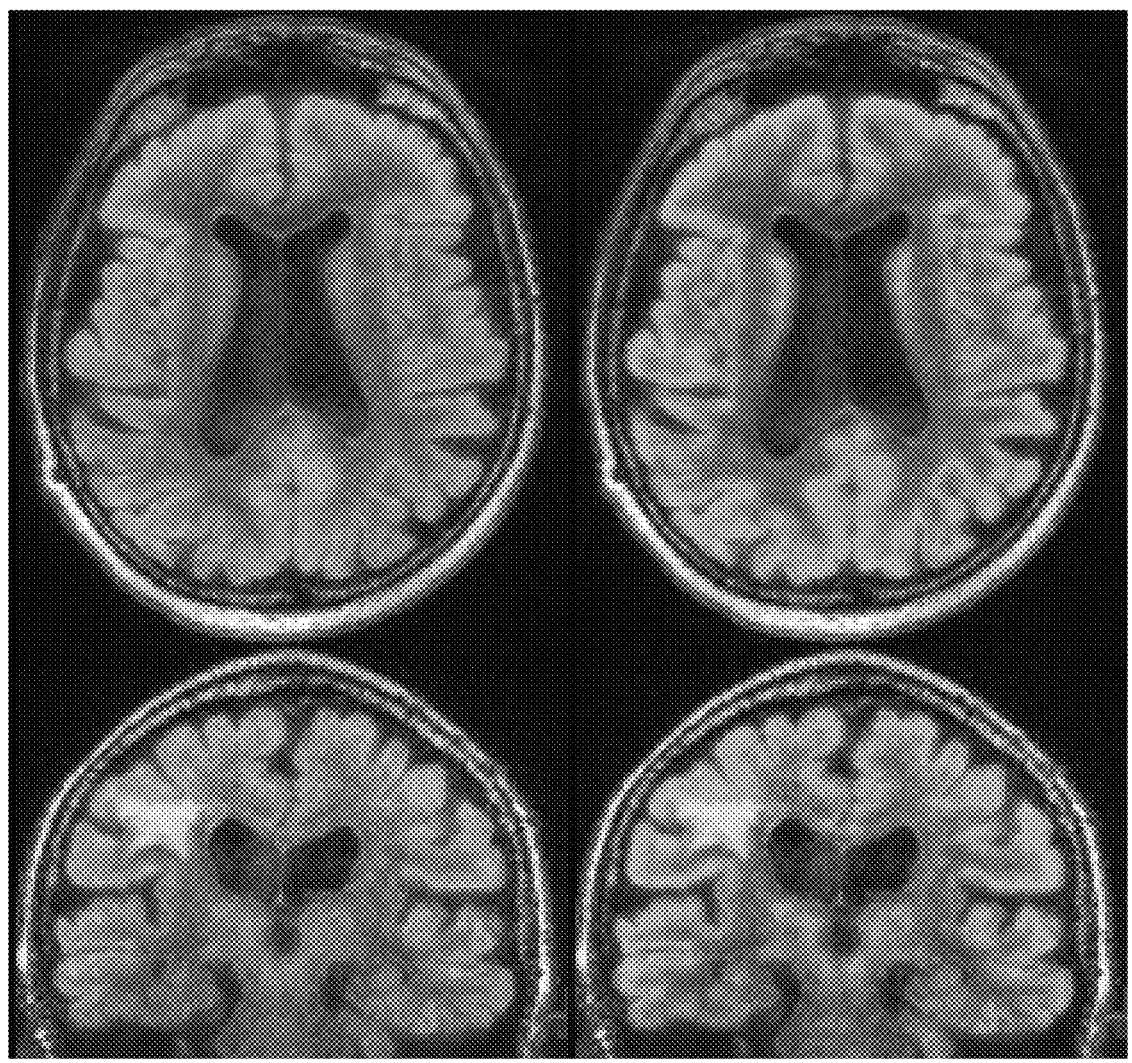
FIG. 3 is an image grid comparing fused PET and MR brain images using TOF-OSEM and MRgTOF-BSREM.

FIG. 3 shows fused PET and MR brain images using TOF-OSEM with 2.78 mm slice thickness (left column) and MRgTOF-BSREM with 1.17 mm slice thickness (right column). Axial (AX) and coronal (COR) planes are shown in each column. The MRgTOF-BSREM images show a higher spatial resolution and are not impacted by the MR lesion. Even though there is a lesion on MR images, it has not impacted the PET images reconstructed by MRgTOF-BSREM due to the construction of the feature space. MRgTOF-BSREM shows higher spatial resolution compared to TOF-OSEM as expected.

Example 2

Two subjects were injected with 5 mCi of RM2 and after 45 min uptake time, they underwent a 20 min prostate exam on SIGNA PET/MR (GE Healthcare, Waukesha). T2 CUBE and DWI were acquired simultaneously with PET. The PET images were reconstructed with TOF-OSEM with isotropic with 2.34×2.34×2.78 mm$^3$ resolution (256×256 matrix on a 60 cm FOV). They were also reconstructed using the anatomical priors i.e. 3D T2 CUBE and DWI images, with MRgTOF-BSREM with isotropic 1.17 mm$^3$ resolution (512×512 matrix on a 60 cm FOV).

FIG. 4A and FIG. 4B show the fused PET and MR prostate images of two subjects, respectively, in axial, coronal and sagittal planes, comparing the conventional TOF-OSEM with 2.34×2.34×2.78 mm$^3$ spatial resolution (left column) and MRgTOF-BSREM with improved 1.17×1.17× 1.17 mm$^3$ spatial resolution (right column).

MRgTOF-BSREM shows better spatial resolution and improved SNR compared to TOF-OSEM in both brain and prostate exam. Because MRgTOF-BSREM uses the feature space and incorporate a conventional PET image reconstruction into the feature space, it is not vulnerable to mismatches between the MR images and true activity distribution.

Figure 6:
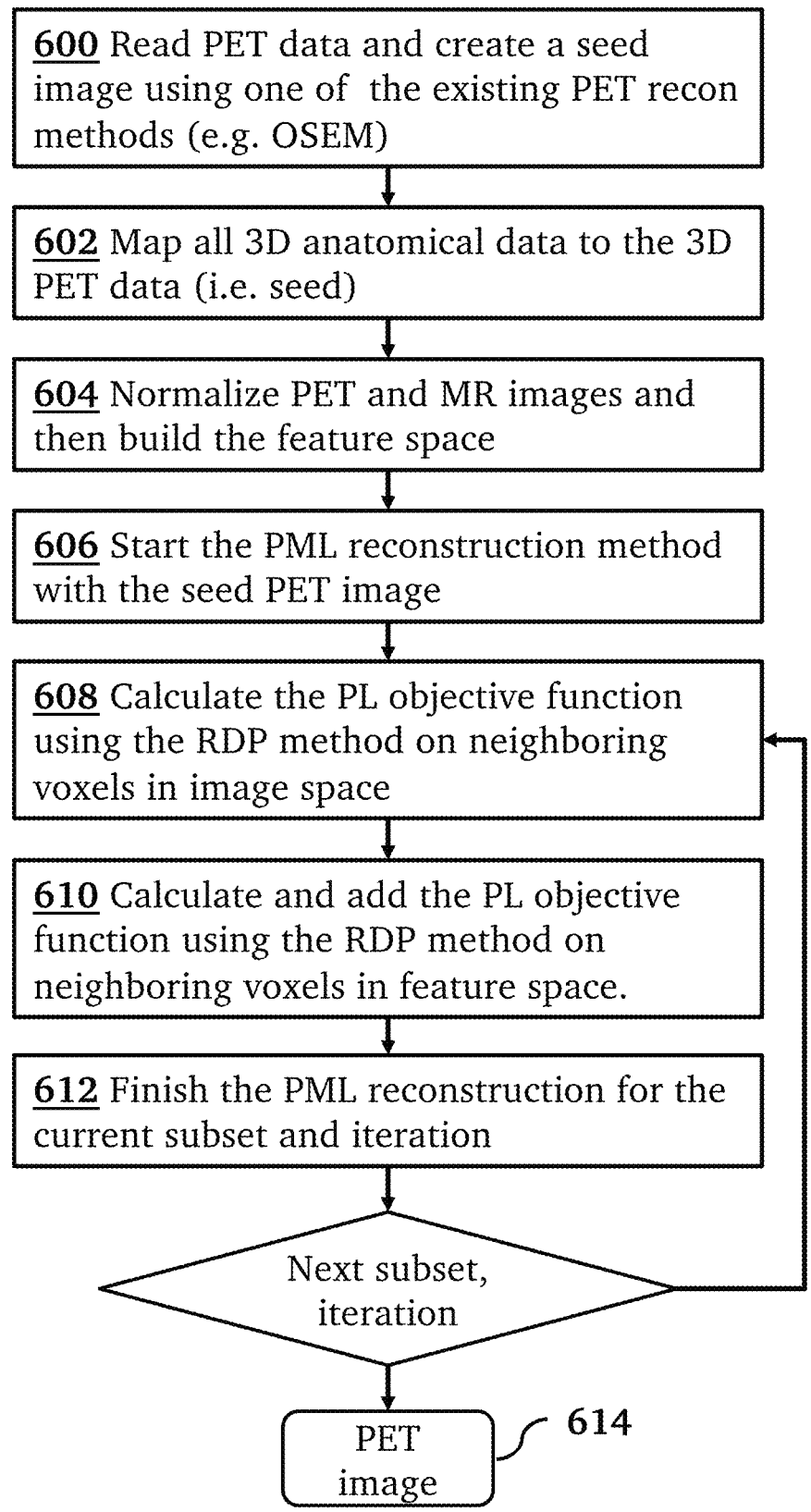
FIG. 6 is a flowchart illustrating steps of a method for PET image reconstruction, according to an embodiment of the invention.

FIG. 6 is a flow chart providing further details of the PET reconstruction method according to an embodiment of the invention. In step 600, PET data is acquired from a PET scan and a seed 3D PET image is created using a conventional PET reconstruction method (e.g. OSEM). In step 602, 3D anatomical data from a conventional MR scan is mapped (i.e., co-registered) to the seed 3D PET image. In step 604, PET and anatomical images are normalized (e.g. normalized to the mean intensity of all tissues within each imaging set), and then a feature space is built from a combination of PET and anatomical imaging sets. To form the feature space, each voxel is mapped into an (N+1)-dimensional space where N is the number of anatomical priors imaging sets, using its values on each normalized imaging set. In step 606, an iterative PML reconstruction method is initialized with the seed PET image. In step 608, a PL objective function is calculated using the RDP method on neighboring voxels in image space as disclosed in Lantos J, et al., Am J Nucl Med Mol Imaging. 2018; 8(2): 110-118. In step 610 a PL objective function using the RDP method on neighboring voxels in feature space (not in image space) is calculated and added to the PL objective function in image space:

$$-\sum_{j=1}^{n_v}\sum_{k\in N_j} W_j W_k \frac{(x_j-x_k)^2}{x_j+x_k+\gamma|x_j-x_k|} - \sum_{j=1}^{n_v}\sum_{k\in F_j}\omega_j\omega_k\frac{(x_j-x_k)^2}{x_j+x_k+\gamma|x_j-x_k|}$$

where $n_v$ is the number of all voxels, $N_j$ is the neighbors of voxel j in image space, $F_j$ is the neighbors of voxel j in feature space, and $W_j$, $W_k$, $\omega_j$, $\omega_k$ are local penalty weights, and y controls the level of edge-preservation.

In step 612, the PML reconstruction for the current subset and iteration is completed by updating the image using the combined PL objective functions. Steps 608, 610, and 612, are repeated for all subsets and iterations (e.g., 28 subsets and 8 iterations), resulting in a final reconstructed image 614.

In MRgBSREM, the number of anatomical series is not limited, and any co-registered anatomical images (e.g., MR, CT) can be used to form the feature space. Any existing methods in forming the feature space or calculating the weights between each voxel and their neighbors can be used within this framework. For instance the images could be normalized differently (e.g. normalized to the intensity of a specific tissue instead of all tissues) and weights could be derived from either L1 or L2 norm of the distance between each voxel and its neighbors.

Any existing methods to update the penalty function (besides the RDP method that was suggested in step 610) in a PML reconstruction method based on neighboring voxels can be used.

This method can be combined with any motion correction method. Since it generates high resolution images, combining it with motion correction will improve the overall image quality. Whether the motion is captured by an external camera or estimated from the PET short frames, or the motion correction is done through List-mode reconstruction (as disclosed in Spangler-Bickell M, et al., IEEE Tran on Radiation and Plasma Medical Sciences 3 (4), 498-503.) or by registering and averaging short PET frames, the proposed method can be used to reconstruct the short PET frames with anatomical priors or use it directly within the List mode reconstruction.

To accelerate the reconstruction, this method can be combined with any AI method (such as Deep Learning and Convolutional Neural Networks). After training the AI module will get the PET seed image along with anatomical images and will perform the 3D high-res PET reconstruction. For instance, the reconstructed images using anatomical priors by this method could be used as the ground truth to train a convolutional neural network with anatomical priors and PET images as its input to generate high-resolution PET images at its output.

The invention claimed is:

1. A method for PET image reconstruction comprising:
   acquiring PET data by a PET scanner;
   reconstructing from the acquired PET data a seed PET image;
   building a feature space from the seed PET image and anatomical images co-registered with the seed PET image;
   performing a penalized maximum-likelihood reconstruction of a PET image from the seed PET image and the feature space using a penalty function calculated based on differences between each voxel and its neighbors both in the PET image and in the feature space;
   wherein building a feature space comprises mapping values of voxels into an (N+1)-dimensional space, where N is a number of sets of the anatomical images.

2. The method of claim 1 wherein the penalty function is a combination of a first PL objective function calculated using a relative difference prior method on neighboring voxels in image space and a second PL objective function using the relative difference prior method on neighboring voxels in the feature space.

3. The method of claim 1 wherein the anatomical images are computed tomography images or magnetic resonance images.

4. The method of claim 1 wherein reconstructing the seed PET image uses OSEM PET reconstruction.

5. A method for PET image reconstruction comprising:
acquiring PET data by a PET scanner;
reconstructing from the acquired PET data a seed PET image;
building a feature space from the seed PET image and anatomical images co-registered with the seed PET image;
performing a penalized maximum-likelihood reconstruction of a PET image from the seed PET image and the feature space using a penalty function calculated based on differences between each voxel and its neighbors both in the PET image and in the feature space;
wherein the penalty function is a combination of a first PL objective function calculated using a relative difference prior method on neighboring voxels in image space and a second PL objective function using the relative difference prior method on neighboring voxels in the feature space.

\* \* \* \* \*